United States Patent [19]
Redziniak et al.

[11] Patent Number: 5,686,103
[45] Date of Patent: Nov. 11, 1997

[54] LIPOSOMAL PRODUCT WITH A LIGAND HAVING FUCOSE AS A TERMINAL MOIETY

[75] Inventors: Gérard Redziniak, St Cyr en Val; Dominique Cerdan, Sully-sur-Loire; Claudine Kieda, Orleans; Michel Monsigny, Saint-Cyr-en-Val, all of France

[73] Assignee: Parfums Christian Dior, Paris, France

[21] Appl. No.: 717,976

[22] Filed: Sep. 23, 1996

Related U.S. Application Data

[60] Continuation of Ser. No. 221,252, Mar. 31, 1994, abandoned, which is a division of Ser. No. 861,780, Apr. 2, 1992, Pat. No. 5,332,575.

Foreign Application Priority Data

Oct. 3, 1991 [JP] Japan ............... 3-283587

[51] Int. Cl.⁶ ............................................. A61K 9/127
[52] U.S. Cl. ................................... 424/450; 424/401
[58] Field of Search .......................... 424/450, 401, 424/63, 489, 499; 514/25 B, 25, 54, 844; 435/7.21; 536/1.1, 4.1, 124

[56] References Cited

U.S. PATENT DOCUMENTS

| | | | |
|---|---|---|---|
| 4,971,795 | 11/1990 | Longenecker | 424/93 |
| 5,108,759 | 4/1992 | Ranney | 424/493 |
| 5,164,182 | 11/1992 | Meybeck | 424/195.1 |
| 5,210,078 | 5/1993 | Toyokuni | 514/54 |
| 5,211,937 | 5/1993 | Brandley | 424/1.1 |

OTHER PUBLICATIONS

Danguy. Eur. J. Bas. Appl. Histochem. 35, p. 341, 1991.

*Primary Examiner*—Gollamudi S. Kishore
*Attorney, Agent, or Firm*—Ostrolenk, Faber, Gerb & Soffen, LLP

[57] ABSTRACT

The invention concerns a method of binding a product to the membrane of a melanocyte by means of a ligand-receptor bond, which comprises using a product consisting of a basic structure coupled to at least one ligand consisting of an oside residue accessible to the membrane receptors, said oside residue being a fucose residue, notably an Alpha-L-fucose residue.

40 Claims, 1 Drawing Sheet

Unstimulated melanoma cell
OAG stimulated melanoma cell

A Incubation at 4°C
B Incubation at 37°C
C Incubation at 37°C + monensin

BSA: bovine serum albumine
Rha: fluorescent alpha-L-rhamnosyl-BSA
GalGP: * * G-phospho-beta-D-galactosyl-BSA

5,686,103

LIPOSOMAL PRODUCT WITH A LIGAND HAVING FUCOSE AS A TERMINAL MOIETY

This application is a continuation of application Ser. No. 08/221,252, filed Mar. 31, 1994, now abandoned, which is a division of application Ser. No. 07/861,780 filed Apr. 2, 1992, now U.S. Pat. No. 5,332,575.

The present invention relates essentially to a method of targeting melanocytes with a compound containing a fucose residue. More specifically, the present invention relates essentially to a method of binding a product to the membrane of a melanocyte by means of a ligand-receptor bond, containing a fucose residue, the method of preparing such a product, to the product obtained, to a cosmetic of pharmaceutical composition in which this product is present with a method of preparation of same and a method of treatment of melanocytes.

The existence of processes for the recognition of cells, for example in relation to other cells or substances such as proteins, has been known for a long time. These processes act by way of a reaction between a ligand and a receptor present on the surface of the cells.

For example, the recognition of surface antigens by monoclonal antibodies is known, this phenomenon being utilized in therapeutic or diagnostic applications. There may be cited, for example, French patent document A1-2 606 034, which describes antibodies capable of recognizing a new surface protein and of being used especially as reagents in techniques based on the antigen-antibody reaction.

Recognition processes are also known which involve sugars. These are recognized specifically by membrane receptors. However, the sugars recognized are not the same from one type of cell to another. It is known, for example, that rat hepatocytes specifically recognize galactose (Ashwell G. and Morell A. G., Advan. Enzymol. (1974) 41, 99–128) whereas humuan fibroblasts recognize mannose-6-phosphate.

Based on this acquired knowledge, attempts have been made to develop targeted drug delivery systems making it possible to reach those cited in the organism on which it is desired to act. Liposomes have been used in particular for this purpose.

Since their discovery by BANGHAM (J. Mol. Biol., 13, 238–252 (1965)); liposomes have been used as vehicles for medicinal or other active principles (see, for example, French patent documents A-2 221 122, A-2 415 460 or A-2 540 381).

French Patent document A-2 609 397 relates to the use of a substance or composition of carbohydrate type as the active principle of a dermatological, cosmetological, pharmaceutical or cell stimulating composition for the purpose of boosting the cell or tissue bioenergetic potential (see claim 1) for improving skin comfort, by virtue of their moisturizing, smoothing and softening effect (page 3, line 33 to page 4, line 10, where even an antiinflammatory action is indicated).

Said document therefore concerns a general teaching which does not relate to the particular problem of melanocytes.

Patent document PCT/WO 87/05300 to BIOCOMPATIBLES LTD relates to a method of preserving a material having a water-dependent structure, which comprises bringing the material into contact with an aqueous solution of a polyhydroxyl compound and then removing the water from this material, the object being to permit the long-term preservation of biological materials such as hemoglobin, erythrocytes, liposomes and cells (see page 1, lines 1 to 4).

Said document concerns the problem of the drying of proteins from aqueous solutions containing saccharides in order to avoid chemical and physical degradation processses (see page 3, 2nd complete paragraph).

More recently, it has been proposed to give liposomes specificity (see BARBET J. et al., "Monoclonal Antibody covalently coupled to liposomes: Specific Targeting to Cells" in J. Supramol. Struct. Cell. Biochem., 16, 243–258 (1981), and LESERMAN L. D. et al., "Targeting to Cells of fluorescent Liposomes covalently coupled with Monoclonal Antibodies or protein A" in Nature, 228, 602–604 (1980).

Furthermore, patent document WO 88/00474 describes a lipid membrane structure comprising a lipid vesicle encapsulating a drug, and a ligand containing a residue specific for hepatobiliary receptors, for the purpose of directing the structure towards the hepatocytes with an exceptional efficacy.

European patent document A-O 028 917 relates to lipid vesicles carrying hydrocarbon surfaces as lymphatically targeted vehicles for therapeutic and diagnostic purposes. Said document does not concern the targeting of melanocytes.

European patent document A-O 285 178 relates to mannobiose derivatives which are useful as a component for modifying pharmaceutical preparations, such as liposomes, having a specific affinity for the Kupffer cells of the liver.

The abstract of STN database of KARLSRUHE, vol. 106, of 8th Jun. 1987, abstract 193579j, cites an article by TODA, in Journal of Investment Dermatology, 88(4), 412–417, which deals with the culture of freshly isolated human keratinocytes on substrates bound to a different ligand, including fibronectin, collagen or a structure membrane.

Said document goes in a totally different direction from that forming the subject of the invention.

In fact, said document recommends a specific culture of the keratinocytes in order to activate them with a view to activating their capacity to multiply on all substrates coated with ligands.

This article demonstrates that the invention described below was not at all evident to those skilled in the art.

Finally, patent application PCT/WO 86/05789 to BIOCARB also relates to hydrocarbon derivatives in the context of specific targeting for a therapeutic or diagnostic purpose, this targeting being effected on molecules of different organs of mammals, including man (see page 1, lines 4 to 8).

It is apparent from the objects indicated on page 2 that the invention described in said document relates to the detection of pathogenic bacteria by particular receptors.

This therefore has nothing at all to do with the problem of the targeting of melanocytes, which is the subject of the invention described below.

As far as the skin is concerned, it is seen that there is an obvious advantage in dermatological and especially cosmetic products, applied locally, binding preferentially and specifically in the epidermis. Binding to the membrane receptors of the melanocytes, which are the essential cells of the epidermis, constitutes a solution to the problem.

Now, no sugar receptors on the surface of melanocytes were known hitherto.

According to the present invention, it has been discovered, totally unexpectedly, that a product can be bound to the membrane of a melanocyte by means of a ligand-receptor bond when using a product carrying at least one ligand consisting of a fucose residue, notably an alpha-L-fucose residue. It has in fact been discovered, unexpectedly, that fucose, and notably alpha-L-fucose, is a specific ligand for the receptor sites of the membrane of melanocytes.

Moreover, it has also been demonstrated that the product carrying this sugar forming a specific ligand for the receptors of the membrane of melanocytes can take a variety of forms. For example, it can be a submicroscopic particle such as a liposome or a polymeric nanoparticle, or a molecule or macromolecule of natural or synthetic origin, such as a protein. Also, the sugar forming the ligand can be coupled in various ways to the surface of this product. It can advantageously be coupled by a covalent chemical bond, preferably via a spacer arm.

Thus the object of the present invention is to solve the new technical problem which consists in providing a solution making it possible specifically to bind a product to the membrane of melanocytes by means of a ligand-receptor bond, if appropriate at the expense of other categories of cells surrounding the melanocytes.

The object of the present invention is to solve the above new technical problem by means of an extremely simple, rapid, practical and reliable method. A further object of the present invention is to solve this new technical problem by providing a method of selecting a product capable of binding specifically to the membrane of a melanocyte by means of a ligand-receptor bond, said method being particularly simple, rapid, practical and reliable.

A further object of the present invention is to solve the afore-mentioned new technical problem by providing a method of preparing such a product capable of binding specifically to the membrane of a melanocyte by means of a ligand-receptor bond, said method also being simple, rapid, practical and reliable. A further object of the present invention is to solve the aforementioned new technical problem by providing a product capable of binding specifically to the membrane of a melanocyte by means of a ligand-receptor bond, said product being in a form which is particularly easy to handle, being reliable and being able to be used rapidly without requiring particular steps. A further object of the present invention is to solve the aforementioned new technical problem by providing a cosmetic or pharmaceutical composition, especially a dermatological composition, and its method of preparation, incorporating such a specific product, which has all the afore-mentioned decisive technical advantages relating to the reliability of the specific binding to the membrane of a melanocyte by means of a ligand-receptor bond using a rapid and practical method.

The present invention solves the aforementioned technical problem by providing the aforementioned solutions in an extremely simple manner which can be used on the industrial scale.

Thus, according to a first feature, the present invention provides a method of binding a product to the membrane of a melanocyte by means of a ligand-receptor bond, which comprises using a product consisting of a basic structure coupled to at least one ligand consisting of an oside residue accessible to the melanocyte membrane receptors, said oside residue being a fucose residue, notably an alpha-L-fucose residue.

According to one advantageous characteristic, the ligand is coupled to the surface of said basic structure by a covalent chemical bond.

According to another advantageous characteristic of the method according to the invention, the ligand is coupled to the surface of the afore-mentioned basic structure via a spacer arm such as the residue of a heterobifunctional reagent or a carbohydrate chain such as Gal(alpha 1-3)Lac or Gal(1-3)GalNAc(1-4)Gal1-4)Glc moiety. Such spacer arms are well known to those skilled in the art, who will be able to refer for example to the article by J. S. Slama and R. R. Rando in Biochemistry, 1980, 19, 4595–4600.

According to another particularly advantageous characteristic of the method according to the invention, the afore-mentioned basic structure is a microscopic or submicroscopic particle such as a liposome or a polymeric nanoparticle.

According to yet another particularly advantageous characteristic of the method according to the invention, the afore-mentioned product is a molecule or macromolecule of natural or synthetic origin, such as a fuco lipid, in particular a ceramide oligosaccharide having an alpha-L-fucose residue as terminal group of the carbohydrate chain, notably a fucolipid extracted from hog gastric mucosa (Slomiany B. L. et al., European Journal of Biochemistry, 1974, 43, 161–165) or from Boar testis (Suzuki A. et al; Journal of Biochemistry (Tokyo) (1975), 78, 947–954).

a fucopeptide, a fucoprotein, notably a neoglycoprotein obtained for example by combining a serum albumin (SA), for example bovine or human serum albumin, with fucose, notably alpha-L-fucose.

Accordingly, another particularly advantageous feature of the method according to the invention, bilayers of the said liposome contain a lipid bearing a fucose residue, notably an alpha-L-fucose residue, said fucose residue being advantageously situated at the end of the spacer-arm such as defined above. For example, the above-said lipid may be a fucolipid, in particular a fucosylated ceramide oligosaccharide such as defined above.

Fucose residues, which are present at the surface of the liposome, because of their hydrophilic character, especially when born at the end of a carbohydrate chain, are thus easily accessible to the melanocytes membrane receptors.

According to another characteristic of the method according to the invention, the afore-mentioned product is or contains a substance of cosmetic or pharmaceutical interest, especially dermatological interest, such as an agent for modulating the metabolism of melanocytes.

According to a second feature, the present invention also provides a method of selecting a product which is to be bound to the membrane of a melanocyte by means of a ligand-receptor bond, which comprises selecting, from a group of products, those consisting of a basic structure coupled to at least one ligand consisting of an oside residue accessible to the melanocyte membrane receptors, said oside residue being a fucose residue notably an alpha-L-fucose residue.

According to a third feature, the present invention also provides a method of preparing a product which is to be bound to the membrane of a melanocyte by means of a ligand-receptor bond, which comprises coupling a corresponding basic structure to at least one ligand consisting of an oside residue accessible to the melanocyte membrane receptors, said oside residue being a fucose residue, notably an alpha-L-fucose.

According to one particularly advantageous characteristic, the afore-mentioned ligand is coupled to the basic structure by a covalent chemical bond. The coupling can be effected in accordance with the general method described by Mac Broom in Methods in Enzymology (1972) 28, 212–222, or else the method described by F. J. Martin and D. Papahadjopoulos in The Journal of Biological Chemistry (1982), vol. 257, N° 1, pages 286–288.

According to another advantageous characteristic of the method according to the invention, the afore-mentioned ligand is coupled to the basic structure via a spacer arm such as defined above.

According to yet another advantageous characteristic of the method according to the invention, the basic structure is a microscopic or submicroscopic particle such as a liposome or a polymeric nanoparticle.

According to yet another particularly advantageous feature of the method according to the invention, bilayers of the said liposome contain a lipid bearing a fucose residue such as defined above, for example a fucolipid.

According to yet another characteristic of the method according to the invention, the afore-mentioned basic structure is a molecule or macromolecule of natural or synthetic origin, such as a protein, for example a serum albumin or a lipid.

According to yet another advantageous characteristic of the method according to the invention, the afore-mentioned product is or contains a substance of cosmetic or pharmaceutical interest, especially dermatological interest, such as an agent for modulating the metabolism of melanocytes.

According to a fourth feature, the invention also covers a product which is to be bound to the membrane of a melanocyte by means of a ligand-receptor bond, said product being obtained by any one of the methods defined above. The invention also covers the novel products capable of binding to the membrane of a melanocyte by means of a ligand-receptor bond, said products comprising at least one ligand consisting of an oside residue accessible to the melanocyte membrane receptors, said oside residue being a fucose residue, notably an alpha-L-fucose residue, coupled to a basic structure selected for example from the group consisting of a microscopic or a submicroscopic particle such as a liposome or a polymeric nanoparticle, a molecule or macromolecule of natural or synthetic origin, such as a lipid or a protein, in particular a serum albumin, and a substance of cosmetic or pharmaceutical interest, especially dermatological interest, such as an agent for modulating the metabolism of the melanocytes.

According to an advantageous characteristic, this coupling takes place via a spacer arm such as the residue of a heterobifunctional reagent or a carbohydrate chain such as Gal(alpha 1-3)Lac or Gal(1-3)GalNAc(1-4)Gal1-4)Glc moiety.

According to yet another particularly advantageous feature of the method according to the invention, bilayers of the said liposome contain a lipid bearing a fucose residue such as defined above, for example a fucolipid.

According to a fifth feature, the present invention also provides a cosmetic or pharmaceutical composition, especially a dermatological composition, which contains at least one product such as obtained by the method described above or such as defined above.

According to an advantageous characteristic of the invention, the afore-mentioned composition is intended for any care or any treatment affecting the melanocytes, for example for acting on the melanogenesis function, for instance stimulating or, on the contrary, inhibiting the melanogenesis activity; for acting on cancerous melanocytes, for instance for treating melanoma; while in such cases the invention product is combined or associated in any way known to one skilled in the art with any cosmetically or pharmaceutically, notably dermatologically, active compound or substance for the said purpose. The substances or compounds are for instance melanogenesis stimulating agents such as tyrosine, forskoline, or protein kinase C stimulating agents, such as linoleic acid or 1-oleyl-2-acetyl-glycerol; melanogenesis inhibiting agents such as tyrosinase inhibiting agents, for instance kojic acid, or protein kinase C inhibiting agents, notably sphingosin; whitening agents, notably retinoic acid or its derivatives, or a carotenoid such as beta-caroten. Among the agents efficient to treat cancerous melanocytes, may be cited methotrexate.

Finally, the invention further relates to a method of preparing a cosmetic or pharmaceutical composition, especially a dermatological composition, wherein at least one product such as obtained by one of the methods described above, or such as defined above, is associated with a cosmetically or pharmaceutically acceptable excipient, vehicle or carrier.

Likewise, the invention also covers a method of care or treatment affecting the melanocytes, for example with a view to act on the melanogenesis, notably stimulating or inhibiting the melanogenesis, to treat melanocytes diseases such as cancer, which comprises applying topically on the areas to be treated, the product such as obtained above by one of the methods described above, or such as defined above, said product being active by itself for said purpose or being combined or associated with any cosmetically or pharmaceutically, notably dermatologically active component or substance in a cosmetically or therapeutically effective amount, said product being advantageously optionally associated with a cosmetically or pharmaceutically acceptable vehicle, carrier or excipient.

It can be seen that the invention makes it possible to achieve the cell targeting of a product, which can thus be concentrated specifically at the melanocytes by virtue of the presence of at least one specific ligand consisting of a fucose residue, notably an alpha-L-fucose residue.

Within the framework of the present invention, the product to which the specific ligand consisting of the fucose residue is coupled is of an arbitrary nature.

It is possible, for example, to use a protein to which fucose is coupled by a synthetic method.

In an advantageous embodiment of the invention, the number of fucose residues, such as defined above, carried by the protein is at least about twenty.

Another basic product which can be used is a submicroscopic particle such as a lipid vehicle, which can be in the form of a liposome.

Within the framework of the present invention, the adjective "lipid" covers all substances comprising a so-called fatty carbon chain generally longer than 5 carbon atoms, this substance normally being called a "lipid".

According to the invention, amphiphilic lipids, i.e. lipids consisting of molecules possessing either an ionic or a non-ionic hydrophilic group and a lipophilic group, are used as the lipid for forming the afore-mentioned liposome, these amphiphilic lipids being capable of forming lipid lamellar phases in particular liposomes in the presence of an aqueous phase.

The following may be mentioned in particular among these lipids: phospholipids, phosphoaminolipids, glycolipids, polyethoxylated fatty alcohols and polyethoxylated or non-polyethoxylated polyol esters. Such substances consist for example of an egg or soya lecithin, a phosphatidylserine, a sphyngomyelin, a cerebroside or an ethoxylated polyglycerol stearate.

According to an advantageous characteristic of the present invention, as far as liposomes are concerned, the proportion of said fucose residue bearing lipid, for instance a fucolipid, as a molar percentage of all the lipid molecules forming the bilayer of the liposome, is comprised between 10% and 100%, and preferably between 15% and 50% relative to all the amphiphilic lipids of the liposome.

It will also be noted that, because of the hydrophilicity of the fucose residues, the latter distribute themselves on the outside of the lipid bilayer of the liposomes, some of them being orientated towards the inside and the others towards the outside of the liposome. It has moreover been observed that the smaller the liposomes are, the greater is the number of fucose residues orientated towards the outside. Thus there is a sufficient number of them to be easily accessible to the melanocyte receptors. It will be understood that this accessibility is even better if the fucose residues are located at the end of a spacer arm.

According to the invention, another basic structure which can be used is a microscopic or submicroscopic polymeric particle such as as a polymer nanoparticle with dimensions generally of less than a micrometer. Preferably polymeric nanoparticles contain $NH_2$ groups, alcohol groups or thiol groups permitting easy coupling with the fucose residue according to the invention. Such particular particles containing $NH_2$ groups are commercially available, for example from Interfacial Dynamics Corporation (Portland, Org.— USA). It is preferable to choose biodegradable nanoparticles, such as polylactates, which are well known to those skilled in the art.

According to a particularly advantageous invention embodiment, particles of the invention are constituted by polymerized fucose obtained by polymerizing fucose in solution, by reaction with epichlorhydrin to reach a fucose gel suspension. Preferably, the fucose gel suspension is further submitted to an homogenization under pressure, e.g. with a well known Manton Gaulin homogenizer, with the purpose of lowering the average particle size.

According to an advantageous characteristic of the present invention, the fucose residues coupled to the surface of said polymeric nanoparticles are alpha-L-fucose residues.

Advantageously the microscopic or submicroscopic particles of the invention are made porous material with the purpose of encapsulating any active substance.

In an advantageous embodiment of the invention, the basic products, such as the afore-mentioned liposomes or nanoparticles, contain one or more substances of cosmetic or pharmaceutical interest, especially dermatological interest, such as an agent for modulating the metabolism of melanocytes, for example enzymatic activity modulators, for example a phosphodiesterase inhibitor such as a xanthine, in particular 3-methylxanthine, or isobutylmethylxanthine (IBMX); an adenylate cyclase activator such as forskoline; a protein kinase C activator such as linoleic acid or 1-oleyl-2-acetyl-glycerol; a protein kinase C inhibitor such as sphingosine; or an anti-cancer agent such as methotrexate.

The basic product which can be used according to the invention can also be the active substance itself of cosmetic or pharmaceutical interest, especially dermatological interest.

Other objects, characteristics and advantages of the invention will become clearly apparent from the following explanatory description with the aid of several Examples of the invention, which are given simply by way of illustration and cannot therefore in any way limit the scope of the invention. In the Examples, all the percentages are given by weight, unless indicated otherwise.

EXAMPLE 1 according to the invention

Preparation of liposomes carrying fucose residues

A. Coupling of alpha-L-fucose to a phospholipid

The coupling between a molecule of dipalmitoylphosphatidylethanolamine (DPPE) and a molecule of alpha-L-fucose (Fuc) is effected by reacting p-phenylisothiocyanato-alpha-L-fucopyranoside (PPITC-alpha-L-fucopyranoside), commercially available by SIGMA (France), with the amine group of DPPE.

The PPITC-alpha-Lfucopyranoside can also be prepared from p-aminophenyl-alpha-L-fucoside by reaction with thiophosgene in accordance with the method described by C. R. McBroom et al. in Methods in Enzymology (1972) 28, 212–222.

The commercial DPPE and the PPITC-alpha-L-fucopyranoside are dissolved in equimolar proportions, at 50° C., in a mixture consisting of a bicarbonate buffer (0.1 M, pH 9.5) and ethanol. The temperature is kept at 50° C. for 3 h, with stirring. The reaction medium is then cooled to about 4° C. and centrifuged.

The solid obtained after washing with distilled water is lyophilized to give a fucosylated DPPE (DPPE-Fuc).

B. Preparation of the liposomes

The following are weighed out:

| | |
|---|---|
| Dipalmitoylphosphatidylcholine (DPPC) | 48.6 mg |
| Cholesterol (chol) | 26.6 mg |
| Dicetyl phosphate (DCP) | 9.1 mg |
| Product according to the invention = DPPE-Fuc | 16.7 mg |

After the afore-mentioned compounds have been mixed in flat-bottomed flask, for example of 100 ml capacity, they are solubilized with a 7/1 chloroform/methanol mixture in accordance with the rotary flask method described by Bangham in J. Mol. Biol., 13, 238–252 (1965). The solvents are then evaporated off at 55° C. under reduced pressure. The traces of solvents can be removed by means of a stream of nitrogen on the "greasy" film formed on the wall of the flask.

10 ml of the aqueous solution to be encapsulated inside the liposomes formed from the afore-mentioned lipid phase are added into the flask. In a particular embodiment, this aqueous solution can for example contain a fluorescent marker consisting for example of the potassium salt of 5-(6)-carboxyfluorescein at a rate of 8 g per 40 ml of distilled water.

An equivalent amount of calcein blue can also be used as a fluorescent marker in another particular embodiment.

After 10 ml of the above aqueous solution to be encapsulated have been added, the mixture is stirred magnetically for 15 to 24 h in the dark.

The formation of large lipid vesicles is observed under the optical microscope.

The contents of the flask are transferred to a 30 ml vessel cooled in melting ice.

Preferably, the suspension is subjected to sonication for three times 2 min at 4° C. and at a power of 200 W, which makes it possible to form liposomes of substantially homogeneous size and of submicroscopic dimensions.

The liposome suspension obtained in this way can be kept at 4° C.

In a preferred embodiment, the liposomes are purified by being separated from the non-encapsulated aqueous phase by gel filtration, as is well known according to the conventioal protocol for the purification of liposomes.

EXAMPLE 2 according to the invention

Preparation of liposomes carrying alpha-L-fucose residues via spacer arms

A. Preparation of alpha-L-D-fucose carrying a spacer arm

An "activated oside" of formula (I):

(I)

consisting of an alpha-L-fucopyranosyl residue in which the OH group located on the first carbon is substituted by a linear chain terminating in an SH group, is prepared as indicated below by carrying out the following successive steps:

Synthesis of 2,3,4-tri-L-acetyl-alpha-L-bromofucopyranoside

The derivative (2) is obtained according to KEMPEN H. J. M. et al., J. Med. Chem. (1984) 27, 1306–1312, by reacting phosphorus bromide PBr3, (7 eq.) and water (50 eq.) with 1,2,3,4-tetra-O-acetyl-alpha-L-D-fucose (1) in acetic anhydride at 0° C., with stirring. The product (2) is recrystallized from a diisopropyl ether/hexane mixture.

Synthesis of 2-L-(2,3,4-tri-O-acetyl-alpha-L-fucopyranosyl)-2-thiopseudourea hydrobromide (3)

The derivative (3) is obtained according to CHIPOWSKY S. et al., Carbohyd. Res. (1973) 31, 339–346, by refluxing a mixture of equimolecular proportions of the derivative (2) and thiourea in anhydrous acetone under argon for 3 h. The product (3) is recrystallized from isopropanol.

Synthesis of 1-(2-carboxyethyl)thio-2,3,4-tri-O-acetyl-alpha-L-fucopyranoside (4)

The product (4) is obtained by reacting equimolecular proportions of the derivative (3) and 3-iodopropionic acid in solution in a 1:1 water/acetone mixture in the presence of 1.15 eq. of $Na_2CO_3$ and 2 eq. of $Na_2S_2O_5$. The reaction is followed by TLC (solvent: AcOEt/AcOH/$H_2O$ 8:2:1).

Synthesis of 1-(2-carboxyethyl)thio-alpha-L-fucopyranoside (5)

The derivative (5) is obtained by deacylating (4) in the presence of 4 eq. of triethylamine and 3 eq. of water in methanol. The reaction is followed by TLC (solvent: AcOEt/AcOH/$H_2O$ 8:2:1); it is complete after 6 days. The deacetylation product is isolated from the reaction medium by passage over a Dowex 1×2 column (HCOO—).

Synthesis of 1-(2-(3-amino-2-hydroxypropylaminocarbonyl)ethyl)thio-alpha-L-fucopyranoside hydrochloride (6)

0.5 g of (5) (1.8 mmol) and 0.8 g of 1,3-di-aminopropan-2-ol (9 mmol) are dissolved in 20 ml of water. The pH of the solution is adjusted to 5.5 (HCl) and 1.2 g of 1-ethyl-3-(3-dimethylaminopropyl)carbodiimide (5.4 mmol) are then added. The reaction is allowed to proceed for 24 h at room temperature, with stirring. The product (6) is isolated from the reaction medium by passage over Dowex 50×2 (Na—) eluents: 0.33 N HCl to detach the monoamines and 2 N HCl to detach the dieunines). The product (6) is finally obtained. Synthesis of the amide formed between the compound (6) and S-acetylthioglycolic acid, (7)

The product (7) is obtained by reacting equimolecular proportions of the derivative (6) and succinimidyl S-actylthioacetate (SATA, synthesized according to Ducan et al., Anal. Biochem. (1983) 132, 68–73) in the presence of triethylamine (1 eq.) in anhydrous dimethylformamide. The product (7) obtained is used in the following operations without particular purification.

Deprotection of the thiol group of the compound (7): synthesis of the derivative of formula (I)

A thiol group is generated on the product (7) (1 eq.), under argon, with the aid of a large excess of hydroxylamine (50 eq.) in a 0.15 M aqueous solution of EDTA, pH: 7.5. The reaction is followed by spectrophotometric determination of the thiols using Ellman's reagent in accordance with the method of P. W. RIDDLES et al., Anal. Biochem. (1978) 94, 75–81. It is complete after 1 h. The resulting product of formula (I) is used quickly for grafting on to the liposomes.

B. Preparation of liposomes carrying maleimide groups

These liposomes are prepared by a conventional method, for example as in Example 1. The composition of the lipid phase is a mixture of the following compounds in molar proportions of 10:2:7:

dipalmitoylphosphatidylcholine (DPPC)
N-/4-(p-maleimidophenyl)butyryl/dipalmitoylphosphatidyl ethanolamine (MPB—DPPE)
cholesterol (chol)

MPB—DPPE is a phospholipid carrying a maleimide group, prepared in accordance with the method described by Martin F. J. and Papahadjopoulos D., J. Biol. Chem. (1982) 257, 286–288, by reacting dipalmitoylphosphatidylethanolamine with succinimidyl 4-p-maleimidophenyl)butyrate (SMPB).

C. Preparation of fucosylated liposomes

The method described by Martin F. J. and Papahadjopoulos D. (reference cited above) is followed.

Thus 6 μmol of the compound of formula (I) prepared in step A are added to 0.67 ml of an aqueous suspension of the liposomes prepared in step B, buffered to pH 6.5.

The mixture is placed under an argon atmosphere for 12 h at ordinary temperature, with gentle stirring.

The thiol group of the compound of formula (I) then binds to the double bond of the maleimide group by means of an addition reaction.

This gives liposomes containing, on the surface, alpha-L-fucopyranosyl residues located at the end of a chain of atoms (spacer arm) corresponding to the chain of the compound of formula (I).

EXAMPLE 3 according to the invention

Preparations of nanoparticles containing fucose residues on the surface

Nanoparticles in the form of beads with a mean diameter of about 0.5 μm, consisting mainly of polystyrene and possessing $NH_3+$ groups on the surface, are commercially available. Such nanoparticles are available for example from Interfacial Dynamics Corporation (I.D.C., Portland, Org., USA).

It is therefore possible by operating in accordance with step A of Example 1, to couple fucose residues to these nanoparticles.

This is done by reacting 0.6 g of these beads with 9 μmol of alpha-L-fucopyranoside phenylisothiocyanate in 5 ml of bicarbonate buffer at pH 9.5 for 5 h at 4° C., with gentle stirring.

The beads are subsequently collected and then rinsed twice with PBS.

This gives nanoparticles containing fucose residues on the surface.

EXAMPLE 4 according to the invention

Preparation of a neoglycoprotein carrying fucose residues.

A protein, for example bovine serum albumin, BSA is used in the present case; about twenty units of fucose are coupled to said protein to give a neoglycoprotein.

This neoglycoprotein, called fucosylated BSA, is obtained by a method based on that described by McBroom et al. in Methods in Enzymology (1972) 28, 212–222.

This method comprises dissolving 250 mg (about 1 mmol) of PPITC-alpha-L-fucopyranoside, prepared as indicated in Example 1, in 2 ml of a 0.15 M aqeuous solution of NaCl and adding 300 g of BSA. The pH is adjusted to 9.0 with NaOH (1 N). After 6 h at room temperature, with stirring the reaction mixture is dialyzed for 16 h at 4° C. against 21 of 0.14 kM NaCl of pH 7.0. The fucosylated BSA is purified further by passage over a Sephadex G25 column (10 ml of gel presaturated with BSA on a column of 0.5×20 cm). The absence of any contamination by free fucose residues is verified by thin layer chromatography. Quantitative analysis of the proteins in conjunction with quantitative analysis of the sugars makes it possible to determine a grafting ratio of 10 to 30 fucose residues per BSA molecule, depending on the preparation in question.

EXAMPLE 5

Determination of the specificity of the products according to the invention towards the membranes of melanocytes.

The specificity of the products according to the invention, carrying oside ligands, towards the membrane of melanocytes could be determined by using fluorescent neoglycoproteins synthesized by the inventors, the endocytosis of which can be observed by various techniques, in particular by the flow cytometry analysis. It should be noted that the endocytosis is the greater, the more the binding at the cell membrane is specific, so that observation of the endocytosis indirectly measures the specificity of the binding of the products according to the invention.

I. MATERIALS AND METHODS

A. Material

RPMI 1640 Gentamycin, fungizone and trypsin were obtained from Gibco-Europe Ltd (Paislay, Scotland); foetal bovine serum from Flow Laboratories (Ayrshire, Scotland, UK). Synthetic melanin and propidium iodide were purchased from Sigma Chemical Co, (Saint Louis, MP USA); ethylenediamine tetraacetic acid (EDTA) from Merck (Darmstadt, FRG); 1-oleoyl-2-acetyl-glycerol (OAG) and monensin from Calbiochem., (La Jolla, Calif., USA). Bovine serum albumine (BSA) was purchased from IBF-Biotechnics (Villeneuve La Garenne, France).

B. Cell Culture

The $C_{32}$ human amelanotic melanoma cell line was kindly supplied by Dr. B. Hommel (Liverpool school of Tropical Medecine, Liverpool, UK). The cells were maintained in culture in RPMI 1640 medium, containing 10% (vol/vol) heat inactivated fetal bovine serum (FBS), 2 mM L-glutamine, 2.5 μg/ml fungizone, and 10 ug/ml gentamycin (hereafter called complete medium), and 5% $CO_2$ 95% air at 37° C. Cells were harvested in logarithmically growing phase using a 0.02% EDTA solution in PBS (w/vol).

C. OAG Stimulation of Pigmentation

OAG is known to induce melanogenesis, notably by human melanocytes, through activation of a protein kinase C (Gordon et al., (1989) 93,700–702).

Melanocytes were seeded at 2.5×10 cells per well of a 6-flat bottomed wells tissue culture plates, 3.5 cm diameter from Falcon (Becton and Dickinson, Grenoble, FRANCE) in culture medium without phenol red. OAG (5 to 300 μM) was added 24 h later. After a 48 h stimulation, dishes were harvested and cell number was determined by using a Mallassez haemacytometer.

To determine melanin content, cell pellet was dissolved in 1 M sodium hydroxide and vortexed vigorously for 15 min. Melanin concentration was calculated by measurement of the optical density at 475 nm with a spectrophotometer (Kontron-Uvikon) and comparison with a standard curve using synthetic melanin (Friedmann and Gilchrest, 1987). Controls were performed with unstimulated cells. The time course of the melanization response following exposure to OAG was determined by an incubation for 12 to 72 h in the presence of OAG at optimal concentration.

D. Neoglycoprotein Synthesis and fluorescein labelling

In example 4, it has been described the preparation of a fucosylated neoglycoprotein, namely Fuc-BSA.

Other glycosylated-BSA were similarly prepared by reaction of a corresponding glycosido-phenyl-isothiocyanate with bovine serum albumin (BSA). These neoglycoproteins were fluoresceinylated by reaction with fluoresceinyl-isothiocyanate isomer I (FITC-1), as previously described by Roche et al., J. Cell. Biochem. (1983), 22, 131–140. The fluorescein-labelled neoglycoproteins (F-neoglycoproteins) were purified by gel filtration on a column of Ultrogel GF 05 from IBF-reactifs (Villeneuve La Garenne, France) in butanol/water (5:95) and then freeze dried.

All neoglycoproteins used contained 20±5 sugar units. The neutral sugar content of a neoglycoprotein was determined by using a resorcinol sulfuric acid micromethod (Monsigny et al., In Anal. Biochem. (1988), 175, 525–530).

The average number of fluorescein residues bound to a neoglycoprotein molecule (F/N ratio) was determined from the absorbance at 495 nm after proteolytic digestion by pronase (Midoux et al., in Cytometry (1987) 8, 327–334 and found to be 2+0.5 for the neoglycoproteins used in these experiments.

E. Binding an internalization of neoglycoproteins by OAG stimulated $C_{32}$ melanoma cells Melanoma cells exponentially growing were stimulated with 100 μM OAG at 37° C. for 24 h; unstimulated cells were used as control. Cells were harvested by 0.02% EDTA in PBS (w/vol), collected by centrifugation, washed in c-PBS and incubated for i h at 37° C. in c-PBS containing 0.2% BSA (w/vol) (c-PBS-BSA). It is indicated that "PBS" means "phosphate buffered saline" pH 7 4, and "c-PBS" means "complete PBS" i e: PBS containing 1 mM $Ca^{++}$ and 0.5 mM $Mg^{++}$ without inhibitor. Then, cells were incubated for 1 h at 4° C. (binding experiments) or 90 min at 37° C. (endocytosis experiments) in the presence of 100 μg/ml of fluorescent neoglycoprotein in c-PBS-BSA. Alpha-L-rhamnosyl (F-, Rha-BSA), 6-phospho-beta-D-galactosyl (F-,6P-Gal-BSA), alpha-L-fucosyl (F-,Fuc-BSA), alpha-D-glycosyl (F-, Glc-BSA), lactosyl (F-,Lac-BSA), N-acetyl-beta-D-glucosaminyl (F-, GlcNAc-BSA) substituted bovine serum albumin were used.

After incubation, cells were washed in c-PBS-BSA and resuspended in c-PBS. Fluorescence quenching upon internalization in acidic compartments was reversed by post-treatment at 4° C. for 30 min in the presence of 50 µM monensin (Monsigny et al., in Biol. Cell 1984 51, 187–136 Midoux et al., in Cytometry (1987 8, 327–334). Monensin allows a more accurate measure of the fluorescence intensity by eliminating masking effect through mainly an increase of pH inside the endocytosis vesicles.

F. Flow cytometry analyses and Sorting

Cells were analyzed by using a FACS 440 (Fluorescence Activated Cell Sorter, Becton and Dickinson, Sunnyvale, Calif., USA). Four parameters were simultaneously recorded for each cell at a rate of 800 cells/s: FSC, forward (or small angle, <12°) scattered light signal, SSC, side (or 90° angle) scattered light signal, and two fluorescence signals FL1, FL2. The 488 nm line of an argon ion laser (Spectra Physics, Moutain View, Calif., USA) was used as excitation beam (laser power is 300 mW). Fluorescence signals were collected using appropriate optical filters for fluorescein emission (BP 530+30 nm) and propidium iodide emission (LP >625 nm). Dead cells were excluded on the basis of red fluorescence emission of DNA-intercaled propidium iodide (Sasaki et al., in Cytometry (1987), 8, 413–420).

Sorting was achieved using a FACS 440. Cells stimulated with 100 uM OAG and harvested by EDTA solution were incubated for 90 min at 37° C. in the presence of 100 ug/ml of alpha-L-fucosyl-BSA. Subpopulation sorting was achieved under the following conditions: rate 1200 cells per second, sort windows set green channel 144 and 255 for FL1 and side scatter channels 55–255 defining large cells, they were set between fluorescence channel 1–132 and side scatter channels 1–28 defining small element population; drop delay was established at 12 ¼ and deflection plate voltage was 2500 volts.

II. RESULTS

Figure 1:
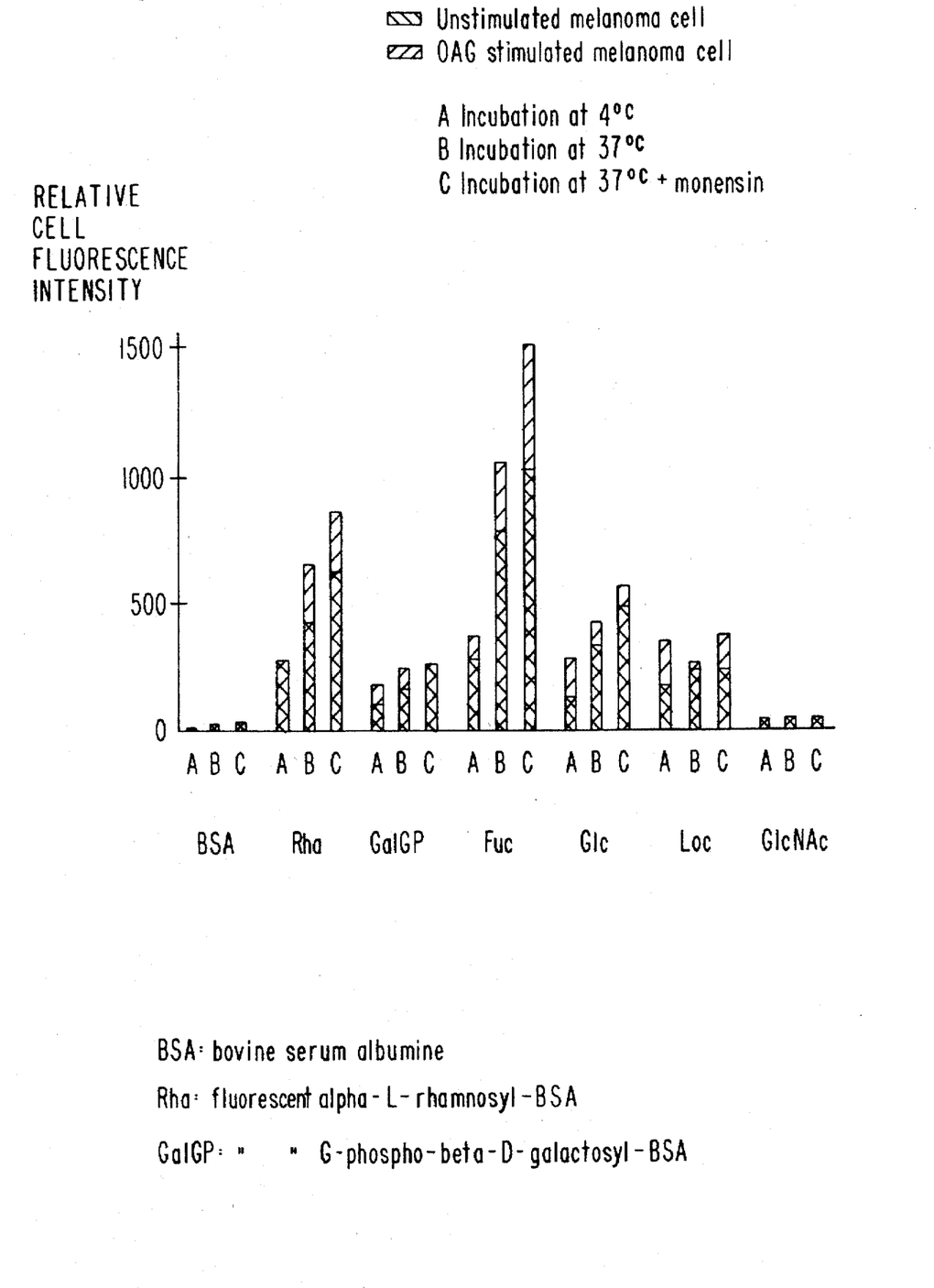
The FIGURE is a representation of the relative fluorescence intensity of stimulated and unstimulated mealanoma cells upon incubation with various glycoproteins.

Membrane lectin expression in $C_{32}$ melanoma cells, modulation during melanogenesis Results given on enclosed single figure show the relative cell fluorescence intensity connected with the extent of endocytosis hence also connected with cell membrane affinity of fluorescent neoglycoproteins for stimulated and unstimulated cells. Glycosylated-BSAs were generally not very efficiently recognized at by melanoma cells excepted at some extent alpha-L-fucosyl-BSA and alpha-L-rhamnosyl-BSA. Fluorescence signals were significantly increased upon incubation at 37° C. only for alpha-L-fucosyl-BASa and alpha-L-rhamnosyl-BSA but the recognition by melanoma cell membranes of alpha-L-glycosyl-BASa appears to be unexpectedly far more important than that of alpha-L-rhamnosyl-BSA. This recognition is further increased after OAG stimulation of melanocytes and its observation is improved by monensin post-treatment.

Accordingly, the expression of these membrane lectins increased upon treatment by OAG in the conditions which increased the melanin content of human melanoma cells.

Also, membrane lectin expression of the second population, characterized by low side and forward scatters, (which predicts small elements), were also analyzed.

This study clearly shows the existence of a specifical affinity of melanocytes membrane receptors for fucose, and in particular alpha-L-fucose. Therefore, it becomes possible to use the invention fucosylated compounds to specifically target melanocytes with the purpose of acting on them, in particular for exerting an action on the melanogenesis function or for treating melanocytes related diseases.

Various Examples of cosmetic or pharmaceutical compositions, especially dermatological compositions, incorporating products according to the invention will now be given.

EXAMPLE 6

Skin tanning cosmetic cream

The cream is obtained by mixing an emulsion and a gelled suspension of liposomes having the following compositions:

| emulsion: | |
|---|---|
| perhydrosqualene | 39.2 g |
| soya lecithin | 0.8 g |
| distilled water | 220.0 g |

| gelled suspension of liposomes: | |
|---|---|
| A - Lipidic phase-components | |
| dipalmitoylphosphatidylcholine (DPPC) | 0.49 g |
| cholesterol (chol) | 0.26 g |
| dicetyl phosphate (DCP) | 0.09 g |
| fucosylated DPPE (Example 1) | 0.16 g |
| forskolin | 0.01 g |
| B - Aqueous phase components | |
| hydrosoluble Coleus Extract | 1 g |
| C - Gelling excipient | |
| neutralized carbopol 940$^R$ | 1 g |
| D - distilled water, perfumes, UV filter | |
| preservatives ad | 100 g |

A mixture of perhydrosqualene (39.2 g) and soya lecithin (0.8 g) is heated in a water bath at 70° C. for 15 min. The oily phase obtained is taken up with 180 ml of distilled water and then emulsified by means of a Raynerie agitator.

In a separate operation, a gelled suspension of liposomes is prepared in the following manner. The liposomes are prepared as indicated in Example 1. The constituents of the lipidic phase A are dissolved in a 7:1 chloroform/methanol mixture in a rotatory evaporator. The resulting organic solution is evaporated in said rotatory evaporator under reduced pressure and the lipid residue is then taken up with 49 g of an aqueous solution made with a part of water D containing the aqueous phase components B to be encapsulated. After sonication, a homogenized suspension of liposomes is thus obtained. Finally, this suspension is gelled by the addition of 50 g of 2% Carbopol 940® gel neutralized with triethanolamine, prepared with the remaining part of water D, which has been prepared in conventional manner.

This tanning cream is applied to the skin areas exposed to sun for improved tanning.

EXAMPLE 7

Lotion for treating gray hair

| Composition: | |
|---|---|
| dipalmitoylphosphatidylcholine (DPPC) | 2.2 g |
| cholesterol (chol) | 1.16 g |
| dicetyl phosphate (DCP) | 0.41 g |
| fucosylated DPPE (Example 1) | 0.73 g |
| IBMX | 0.10 g |
| dibutyryl AMPc | 0.10 g |

-continued

| Composition: | |
|---|---|
| preservative | 0.10 g |
| aqueous excipient gelled with Carbopol 940 ® (at 0.1%) | 100 g |

A lipid powder is prepared according to Example 8 by spray drying a solution in an 8:2 methylene chloride/methanol mixture containing the lipid or hydrophobic constituents.

This powder is then dispersed, by agitation, in 50 ml of distilled water and the dispersion is then homogenized with ultrasound by the method known to those skilled in the art.

This gives a suspension of liposomes containing fucose residues on the surface. Finally, this suspension is mixed with about 45 g of neutralized Carbopol 940® gel prepared in conventional manner.

The resulting lotion can be applied locally on scalp for the treatment of grey hair, twice a day.

EXAMPLE 8

Cosmetic anti melanic blots liposomal gel
A. Preparation of liposomes carrying fucosylated residues via spacer arms The composition of the lipid phase is a mixture of the following compounds:

| fucolipid from hog gastric mucosa | 1 part |
|---|---|
| soya lecithin | 6 parts |
| cholesterol | 0.5 part |
| sphingosine | 1 part |
| dry mulberry root bark extract | 0.5 part |

The fucolipid is prepared according to an isolation method as described by John M. MacKibbin in "Journal of lipid research" (1978) 19, 131–147, particular 133–134 from hog gastric mucosa).

The crude extract of the bark of mulberry root used is an extract marketed by the Japanese company Marusen Seiyaku Co. Ltd. which is in the form of a transparent liquid with a weak characteristic odor, a slightly yellowish brown color, a pH of about 4.4, a density of about 0.95, a proportion of residue after evaporation of about 1.8% by weight/volume.

This mulberry extract is evaporated to dryness, thereby obtaining the dry mulberry root bark extract. The constituents of the lipid phase are dissolved at a concentration of about 10% in a mixture of methylene chloride and methanol (80:20 by volume). The organic solution is spray-dried at about 60° C. in accordance with the method described in U.S. Pat. No. 4,508,703 to give a powder.

This powder is then dispersed by stirring in the aqueous solution to be encapsulated, at a rate of 1 part of powder to 100 parts of aqueous solution. This solution can for example contain a sodium Ascorbate at a concentration of 0.01% by weight in water.

A suspension of liposomes is thus formed which is preferably homogenized, for example by means of a homogenizer under pressure, as described in U.S. Pat. No. 4,621,023.

This gives a suspension of liposomes containing on the surface, fucosylated residues linked to the lipidic bilayer by a spacer arm consisting of Gal(Alpha 1-3)Lac.

B. Preparation of the cosmetic anti-melanic blos liposomal gel

For gelling the aqueous suspension of liposomes, it is admixed with the aqueous suspension of liposomes a gel containing 2.5% of neutralized Carbopol (R) 940 at a relative weight ratio of 1/1.

This cosmetic anti-melanic blots liposomal gel can be applied as such topically to the desired skin areas to be treated.

EXAMPLE 9

Cosmetic Anti-chloasma liposomal gel composition

In a manner similar to that of example 8, except that the dry mulberry root bark extract is replaced by 0.25 part of Beta-Carotene and 0.25 part of vitamin A propionate. Further, in the aqueous phase, sodium ascorbate is replaced by 0.01 weight % of Oraposide and 0.01% of melissa extract commercially available, with respect to the aqueous solution.

EXAMPLE 10

Dermatologic anti-melanoma liposomal gel
Composition:

| A - Lipidic phase component | |
|---|---|
| DL-alpha-dipalmitoyl phosphatidylcholine | 4 parts |
| cholesterol | 3 parts |
| boar testis fucolipids | 3 parts |

B-Aqueous phase
Aqueous solution of methotrexate 0.5% by weight in a $NaHCO_3$ buffer.

1 g of the lipidic phase components A was dissolved in 100 ml of a chloroform: methanol (2:1 v/v) mixture in a pear-shaped flask. The solution obtained was evaporated under vacuum in a rotary evaporator. The remaining lipidic film deposited on the flask wall was then hydrated by introducing in the flask 100 ml of the methotrexate aqueous buffered solution B, and mechanically shaking the flask at 55° C. for 0.5 h, then at room temperature for 1 h.

In that way it was obtained a suspension of liposomes with bilayers at the surface of which were distributed fucose residues situated at the end of spacer arms constituted by carbohydrate chains.

Advantageously, liposome-entrapped methotrexate was separated from free methotrexate, initially by dialysis against 0.5% $NaHCO_3$ buffer for 48 h, and subsequently eluted through a sephadex G-25M column.

The purified liposomal suspension is then gellified by mixing with the same volume of a gelled aqueous excipient containing 0.1% by weight of neutralized Carbopol 940 (R), according to a method well-known by a person skilled in the art. This anti-melanoma liposomal gel may be used in topical applications on melanoma, optionally as part of an anti-cancer treatment program.

What is claimed is:

1. A liposomal product which is the chemical reaction product of a lipid component of a liposome with at least one ligand having fucose as a terminal moiety.

2. The product of claim 1, wherein said chemical reaction comprises coupling said ligand to the outer surface of said liposome by means of a covalent chemical bound.

3. The product of claim 1, wherein said chemical reaction comprises coupling said ligand to the outer surface of said liposome via a spacer arm.

4. The product of claim 3, wherein said spacer arm is a carbohydrate chain.

5. The product of claim 3, wherein said spacer and is selected from the group consisting of: a Cral(alpha 1-3)Lac moiety, and Gal(1-3)Gal NAc(1-4)Gal(1-4)Glc moiety.

6. The product of claim 1, therein said fucose is an alpha-L-fucose.

7. The product of claim 1, wherein said lipid component is combined with said fucose prior to formation of said liposome, thereby being present in the bilayers of said liposomes.

8. The product of claim 7, wherein said lipid component is a fucolipid.

9. The product of claim 7, wherein the proportion of said lipid component combined with said fucose, as a molar percentage of all the lipid molecules, forming the bilayers of the liposome, ranges between 10% and 100% of all the lipids of the liposomes.

10. The product of claim 9, wherein the proportion .of the lipid component combined with said fucose, as a molar percentage of all the lipid molecules forming the bilayers of the liposomes, ranges between 15% and 50% relative to all the lipids of the liposomes.

11. The product of claim 1, wherein said liposome contains at least one substance selected from the group consisting of: cosmetic, and, pharmaceutical.

12. The product of claim 1, wherein said liposome contains at least one substance selected from the group consisting of: a phosphodiesterase inhibitor, an adenylate cyclase activator, a protein kinase C activator and a protein kinase C inhibitor.

13. The product of claim 12, wherein the said phosphodiesterase inhibitor is a xanthine.

14. The product of claim 13, wherein the said xanthine is 3-methylxanthine or isobutylmethylxanthine.

15. The product of claim 12, wherein the said adenylate cyclase activator is forskoline.

16. The product of claim 12, wherein the said protein kinase C activator is quinoleic acid or 1-oleyl-2-acetylglycerol.

17. The product of claim 12, wherein the said protein kinase C inhibitor is sphingosine.

18. The product of claim 11, wherein said pharmaceutical is an anticancer agent.

19. The product of claim 18, wherein said anticancer agent is methotrexate.

20. A cosmetic or a pharmaceutical composition, comprising a liposomal product, which is the chemical reaction product of a lipid component a liposome and at least one ligand having fucose as a terminal moiety, said liposome bearing on its outer surface said fucose.

21. The composition of claim 20, wherein said chemical reaction comprises coupling said ligand to the outer surface of said liposome by means of a covalent chemical bound.

22. The composition of claim 20, wherein said chemical reaction comprises coupling said ligand to the outer surface of said liposome via a spacer arm.

23. The composition of claim 22, wherein said spacer arm is a carbohydrate chain.

24. The composition of claim 22, wherein said spacer arm is selected from the group consisting of: a Gal(alpha 1-3)Lac moiety, and Gal(1-3)Gal NAc(1-4)Gal(1-4)Glc moiety.

25. The composition of claim 20, wherein said fucose is an alpha-L-fucose.

26. The composition of claim 20, wherein said lipid component is combined with said fucose prior to formation of said liposome, and the fucose is ultimately present in the bilayers of said liposomes.

27. The composition of claim 20, wherein said lipid component is a fucolipid.

28. The composition of claim 26, wherein the proportion of said lipid component combined with said fucose, as a molar percentage of all the lipid molecules forming the bilayers of the liposome ranges between 10% and 100% of all the lipids of the liposomes.

29. The composition of claim 28, wherein the proportion of the lipid combined with said fucose as a molar percentage of all the lipid molecules forming the bilayers of the liposomes ranges between 15% and 50% relative to all the lipids of the liposomes.

30. The composition of claim 20, wherein said liposome contains at least one substance selected from the group consisting of a cosmetic and a pharmaceutical product.

31. The composition of claim 20, wherein said liposome contains at least one substance selected from the group consisting of: a phosphodiesterase inhibitor, an adenylate cyclase activator, a protein kinase C activator, and a protein kinase C inhibitor.

32. The composition of claim 31, wherein said phosphodiesterase inhibitor is a xanthine.

33. The composition of claim 32, wherein said xanthine is 3-methylxanthine or isobutylmethylxanthine.

34. The composition of claim 31, wherein the said adenylate cyclase activator is forskoline.

35. The composition of claim 31, wherein the said protein kinase C activator is quinoleic acid or 1-oleyl-2-acetylglycerol.

36. The composition of claim 31, wherein the said protein kinase C inhibitor is sphingosine.

37. The composition of claim 20, wherein said pharmaceutical is an anticancer agent.

38. The composition of claim 37, wherein said anticancer agent is methotrexate.

39. The composition according to claim 20, wherein the chemical reaction is performed between a lipid component having a maleimide group and said ligand.

40. The composition according of claim 22, wherein the chemical reaction is performed between a lipid component having a maleimide group and said ligand.

* * * * *